United States Patent [19]

Fickat et al.

[11] Patent Number: 4,666,641

[45] Date of Patent: May 19, 1987

[54] PREPARATION OF BIODEGRADABLE MICROCAPSULES BASED ON SERUM ALBUMIN

[75] Inventors: René Fickat, Reims; Simon Benita, Puteaux; Francis Puisieux, Maisons-Alfort, all of France

[73] Assignee: Universite Paris-Sud (Paris XI), Orsay Cedex, France

[21] Appl. No.: 741,190

[22] Filed: Jun. 4, 1985

[30] Foreign Application Priority Data

Jun. 5, 1984 [FR] France .................................. 84 08761

[51] Int. Cl.⁴ .......................... A61K 9/52; A61K 9/64; B01J 13/02
[52] U.S. Cl. ........................................ 264/4.3; 264/4.7; 424/491; 424/19; 424/36; 428/402.2; 514/963
[58] Field of Search ................................ 264/4.3, 4.7; 428/402.2; 424/19, 36; 514/963

[56] References Cited

U.S. PATENT DOCUMENTS

| | | | |
|---|---|---|---|
| 3,137,631 | 6/1964 | Soloway | 264/4.7 X |
| 4,107,288 | 8/1978 | Oppenheim et al. | 264/4.3 X |
| 4,115,534 | 9/1978 | Ithakissios | 252/62.53 X |
| 4,147,767 | 3/1979 | Yapel, Jr. | 424/22 |
| 4,251,387 | 2/1981 | Lim et al. | 264/4.7 X |
| 4,331,654 | 5/1982 | Morris | 252/62.53 X |
| 4,419,340 | 12/1983 | Yolles | 424/19 |

FOREIGN PATENT DOCUMENTS

| | | | |
|---|---|---|---|
| 0054396 | 6/1982 | European Pat. Off. | 424/22 |
| 0106610 | 7/1982 | Japan | 424/19 |
| 0076237 | 11/1976 | Luxembourg | 424/22 |
| 795977 | 6/1958 | United Kingdom | 424/37 |

*Primary Examiner*—Richard D. Lovering
*Attorney, Agent, or Firm*—Fleit, Jacobson, Cohn & Price

[57] ABSTRACT

The present invention relates to biodegradable microcapsules based on serum albumin, the preparation thereof and the application thereof to the release of drugs in situ.

A feature of the microcapsules according to the present invention is that their wall consists of serum albumin, a portion of which is crosslinked by interfacial polymerization with the aid of an acylating bifunctional reagent, and the other, non-crosslinked portion of which is denatured by means of an alcohol.

16 Claims, 3 Drawing Figures

PREPARATION OF BIODEGRADABLE MICROCAPSULES BASED ON SERUM ALBUMIN

The present invention relates to biodegradable microcapsules based on serum albumin, as well as to the preparation thereof and the application thereof to the controlled release of drugs in situ.

It is first appropriate to recall that microcapsules are artificial organelles which are used for putting various drugs into galenical form. The inclusion of an active principle in a microscopic spherule makes it possible, in particular, to provide for temporary protection thereof against various denaturing agents, such as digestive enzymes.

In other cases, the wall of the microcapsules enables the diffusion of the active principle to be varied, and this is turned to account in the preparation of delayed action galenical forms. It is thus necessary to provide every assurance that the wall of the microcapsule is harmless in relation to administration in human therapy.

Such requirements are still more stringent when the microcapsules are intended for therapy in situ, such as chemoembolization.

It will be recalled briefly that chemoembolization is a technique the use of which is envisaged in the treatment of certain tumors. According to this technique, the artery feeding the tumor is obstructed by means of an embolism placed in position by catheterization. In chemoembolization, the embolism contains an antitumor substance which diffuses into the tumor tissues.

In the prior art, microcapsules have already been proposed in which the outer wall is obtained by interfacial crosslinking of various proteins, chosen in particular from proteins of natural origin so as to provide high assurance of harmlessness.

Although various attempts have been made in this direction, for example by modifying the nature of the biological macromolecules and their bridging agents which condition the composition and the properties of the wall of the microcapsules, the preparation of spherules completely biodegradable in vivo has never been achieved.

The most successful results appear to be obtained with microcapsules of serum albumin, which, when injected into the renal artery in rats, show good tolerability but far too long a degradation time in vivo.

Such a degradation time, which always exceeds 15 days, causes undesirable systemic side effects, in particular of an inflammatory type, which prohibit the use of such forms of dosage, especially in the field of chemoembolization. An excessively slow degradation of the microcapsules, greater than about 8 days, leads to the formation of irreversible ischemic lesions in the organ located downstream of the feeding artery obstructed by means of microcapsules placed in position by catheterization.

Furthermore, after the microcapsules have remained in the feeding artery for more than about 8 days, the formation of an inflammatory granuloma is observed, giving rise to a type of sclerotic aggregate which considerably reduces the release of the encapsulated active principle.

The present invention had as its precise object the avoidance of these disadvantages, and it was thus envisaged to modify the nature of the walls of the microcapsules in order to lower the degradation time of the microcapsules in vivo to less than 8 days.

This objective was achieved, according to the present invention, by developing biodegradable microcapsules containing a pharmaceutically active substance, wherein the wall of the microcapsules consists of serum albumin, a portion of which is crosslinked by interfacial polymerization with the aid of an acylating bifunctional reagent, and the other, non-crosslinked portion of which is denatured by means of an alcohol.

It is, furthermore, appropriate to specify that, in addition to complete biodegradability, these microcapsules show an excellent capacity for adsorbing active principles, which property has never been obtainable in the prior art.

The present invention also relates to the application of these microcapsules to the controlled release of drugs in situ, especially in the field of chemoembolization.

According to the present invention, the microcapsules are prepared from serum albumin by carrying out the following successive operations:

(a) the serum albumin is emulsified by dispersion in an organic solvent system, by adding a pharmaceutically acceptable emulsifying agent, and stirring;

(b) to the emulsion thereby obtained, maintained stirred, a crosslinking agent dissolved in the said organic solvent system is added, and stirring is maintained until the desired degree of interfacial crosslinking is obtained;

(c) the microcapsules are isolated after dilution of the reaction mixture followed by a succession of stages of washing with suitable solvents and decantation stages, and the microcapsules are then subjected to several washes with alcohol and to immersion in alcohol, preferably absolute, for at least 12 hours in order to denature the non-crosslinked serum albumin, and (d) after the microcapsules are dried, the pharmaceutically active substance is incorporated therein by controlled immersion of the microcapsules in a titrated solution of the said substance.

Other characteristics and advantages of the present invention will emerge on reading the description given below, especially with reference to the attached illustration.

BRIEF DESCRIPTION OF DRAWINGS

in FIG. 2, 1.9 cm represents 200 µ; in FIG. 3, 2.4 cm represents 200 µ).

Figure 1:
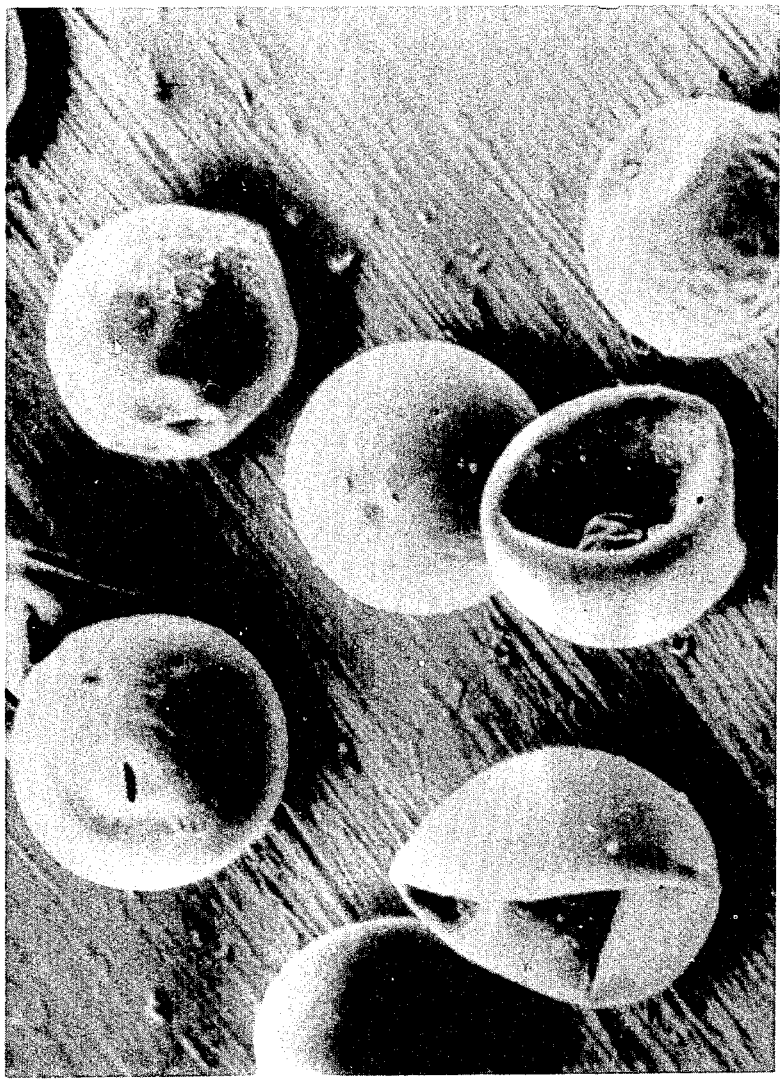
FIGS. 1 to 3 show plates of microcapsules according to the invention seen with the scanning electron microscope (in FIG. 1, 2.2 cm represents 200µ.

The process for preparing the microcapsules according to the present invention is mainly subdivided into 4 successive stages, namely:

(a) emulsification of the serum albumin;
(b) interfacial crosslinking;
(c) isolation of the microcapsules, and
(d) incorporation of the active principle.

In the first stage of emulsification of the serum albumin, the latter is dispersed in an organic solvent system, as a result of adding a pharmaceutically acceptable emulsifying agent and by applying stirring. The serum albumin used is, for example, obtained by lyophilization of a 20% strength human serum albumin solution, and takes the form of a pale yellow powder completely soluble in water.

The organic solvent system used in this first emulsification stage is advantageously chosen in such a way that it is not miscible with water and that the cross-linking agent used in the second stage can dissolve therein. It is beneficial to use, for example, a binary mixture consisting of a chlorinated hydrocarbon containing 1 or 2 carbon atoms, such as chloroform, methylene chloride or trichloroethylene, and a non-chlorinated hydrocarbon containing 5 to 7 carbon atoms, such as hexane or cyclohexane.

The emulsifying agent used in this first stage is a surfactant such as a sorbitan fatty acid ester, or any other surfactant which enables a water-in-oil emulsion to be prepared. Sorbitan trioleate (Span 85 ®) can thus be used. In practice, however, phosphatidylcholine (Epikuron 180 ®) is preferably employed.

The volumes and relative amounts of serum albumin, organic solvents and emulsifying agent for obtaining the emulsion intended for subsequent crosslinking can be adjusted with a fairly wide degree of scope, and can differ significantly from the proportions given subsequently simply by way of an example.

Such an emulsion can be readily obtained simply by stirring, for example by means of a glass anchor driven mechanically inside a centrifuge tube. A speed of rotation of the order of 500 to 1,000 rpm continued for about 1 to 3 minutes then suffices to bring about satisfactory emulsification.

In the second stage, the emulsion thus obtained, maintained stirred, is subjected to interfacial crosslinking. During this stage, the wall of the microcapsules is formed by crosslinking, especially by means of an acylating bifunctional reagent such as a dicarboxylic acid halide or a diisocyanate, in which the two functional groups are both carried on an aromatic ring, or alternatively are separated by an aliphatic chain of 2 to 10 carbon atoms, or one of which is carried on an aromatic ring and the other on an aliphatic chain attached to the ring. Possible examples are succinyl dichloride, sebacoyl dichloride, terephthaloyl dichloride, toluene diisocyanate and hexamethylene diisocyanate.

This crosslinking agent is added to the emulsion in the form of a solution in the same organic solvent system as that used in the first emulsification stage. Ther interfacial polymerization reaction is carried out at a temperature which can be between the freezing point and the boiling point of the liquids used, most frequently at a normal temperature.

As stated above, it appeared that the interfacial crosslinking time had to be between about 30 minutes and about 90 minutes, since completely satisfactory results were obtained in practice with interfacial crosslinking times of the order of 60 minutes.

Furthermore, acccording to an additional characteristic of the present invention, the ratio by weight of the serum albumin to the crosslinking agent is chosen such that:

$$\frac{1}{1.250} \leq \frac{\text{serum albumin}}{\text{crosslinking agent}} \leq \frac{1}{0.2}$$

Within this entire range of relative proportions of serum albumin to crosslinking agent, microcapsules completely biodegradable in vivo are obtained for interfacial crosslinking times of the order of 60 minutes. It is, however, quite evident that the properties of this wall, and indeed its appearance, are modified according to this ratio.

In the third stage of the process of the invention, the microcapsules are isolated from the reaction mixture after the latter has been diluted in order to stop the crosslinking reaction. Whereas in the prior art the operation for isolating microcapsules constituted a stage in which there were no actual problems, the microcapsules which are the subject of the present invention can only be removed from the reaction medium with much more difficulty.

In the prior art, after the stirring had been stopped, the microcapsules were left to settle, and then washed with a solution of Tween 20 ® in 25% strength glycerine and several successive mixtures of water and alcohol. After each wash, the microcapsules were then isolated by filtration or centrifugation, and then dried.

Such a method of separation was suitable for microcapsules in which the wall consisted of a highly crosslinked protein. This wall was, in effect, sufficiently resistant to withstand the successive washes and the centrifugation operation. On the other hand, the partially crosslinked microcapsules which are the subject of the present invention possess a wall of low strength which bursts as a result of the various aqueous washes, and in no case withstands centrifugation.

Thus, it was necessary to make use of a separation method which virtually avoids contact with water, and gravitational shock.

According to the present invention, the microcapsules are isolated from the reaction medium by carrying out the following successive operations:
the supernatant is separated;
at least one washing of the microcapsules is carried out using the said organic solvent system;
⅓ of glycerine containing approximately 20% of polysorbate and then ⅔ of water are added to the microcapsules in that order; and
the microcapsules are separated by simple sedimentation, before the said microcapsules are washed with alcohol and immersed in alcohol.

It is important to add first the glycerine containing the polysorbate, and then the water, to the microcapsules. In effect, the glycerine causes a kind of protective film to form around the microcapsules. During all these separation operations, the microcapsules are stirred to a moderate extent and then separated by sedimentation.

At the end of the preparation, it is essential to wash the microcapsules with alcohol optionally containing a small proportion of water. In practice, a succession of 5 washes with water/alcohol mixtures containing 60%, 70%, 80%, 90% and 95% of absolute alcohol, respectively, leads to complete removal of all traces of residual crosslinking agents.

At this stage, the weakly crosslinked microcapsules are very rapidly degraded in vivo, but are still very highly water-absorbent and burst spontaneously on contact with water.

According to the present invention, the microcapsules thus washed are immersed for at least 12 hours in alcohol, preferably absolute, so as to complete the denaturation of the albumin which has not been crosslinked.

Finally, the microcapsules are separated by evaporating the alcohol, for example in a rotary evaporator at a temperature of the order of 35° C., and the microcapsules are then left, for example at 35° C. for 24 hours in a drying oven, in order to complete drying. The microcapsules thus obtained, even when very weakly crosslinked, then have a strong wall which enables them to be handled easily, and the microcapsules thus obtained have furthermore become completely stable in water.

With reference to the attached illustration, it is observed that the microcapsules can have different morphologies, resulting from different degrees of crosslinking.

Thus, the microcapsules in FIG. 1 result from interfacial polymerization performed with a ratio of serum albumin to crosslinking agent equal to 1/1.250. Their wall surface is smooth. These microcapsules are completely biodegradable, but their degradation time, however, is about 15 days, and this would consequently prohibit their use in chemoembolization.

Figure 2:
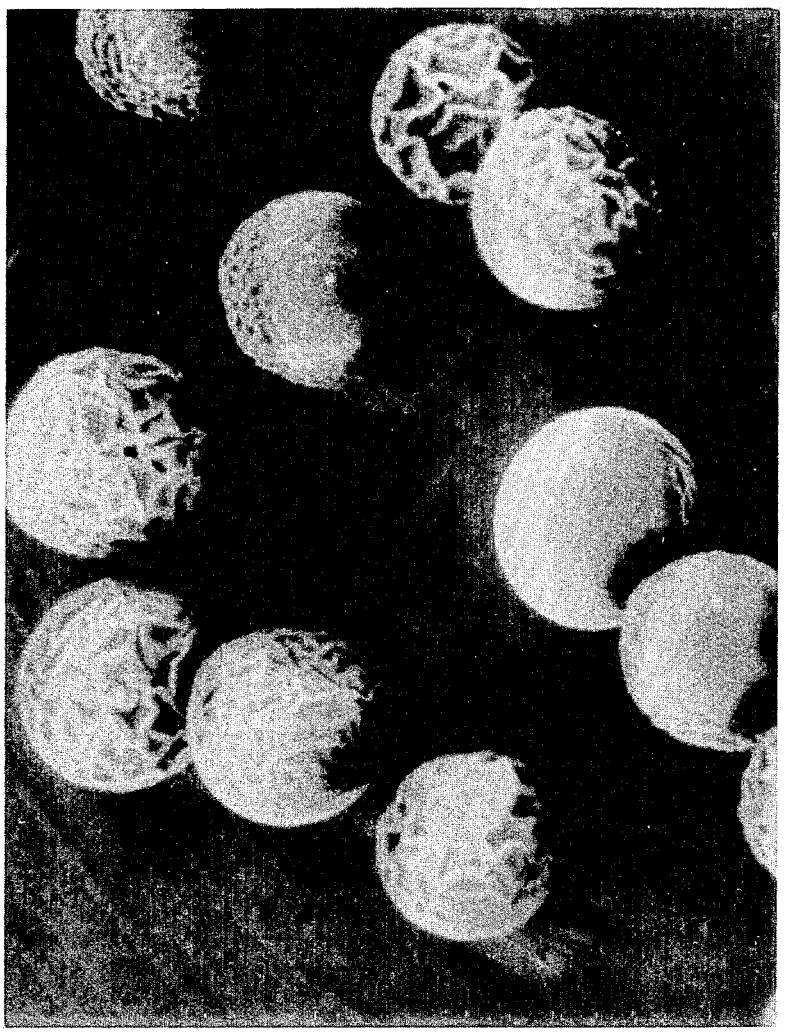
Figure 3:
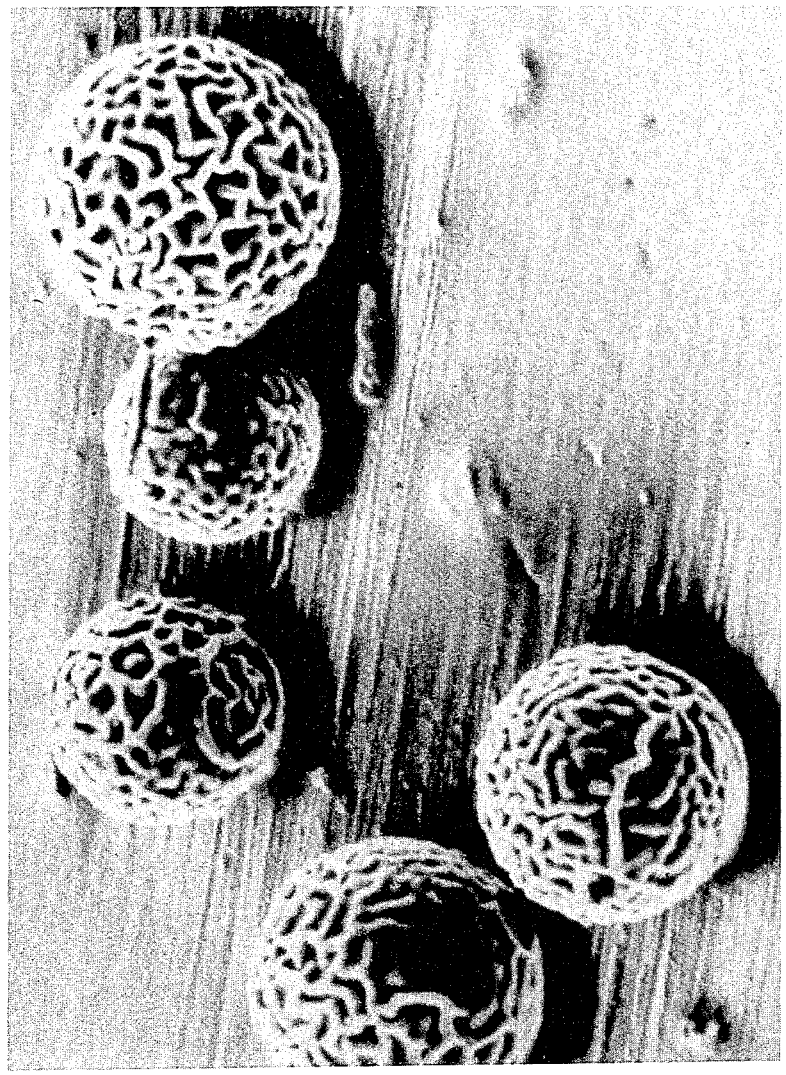

The microcapsules in FIGS. 2 and 3 correspond, respectively, to serum albumin/crosslinking agent ratios equal to:

$$\frac{1}{0.250} \quad \text{(FIG. 2)}$$

and $$\frac{1}{0.200} \quad \text{(FIG. 3)}$$

These microcapsules have a rough wall of wrinkled appearance, which results from the microcapsules staying in the alcohol which denatures the non-crosslinked regions. In this connection, it will be specified that the weakly crosslinked microcapsules have an initial yellow appearance before their immersion in the alcohol, whereas after immersion they become white.

The microcapsules thus obtained are advantageously subjected to a sterilization operation, for example a radiosterilization by application of radiation of approximately 2.5 Mrad.

Analysis of the microcapsules thus obtained shows that all the crosslinking agent has been removed, whereas in the case of the microcapsules of the prior art, a small amount of crosslinking agent is always retained on the walls of the microcapsules.

Within the context of the present invention, the complete removal of the crosslinking agent is at least partly due to the prolonged immersion of the microcapsules in alcohol.

EXAMPLE OF PREPARATION OF MICROCAPSULES 1000 mg of lyophilized human serum albumin are dissolved in 3 ml of an $Na_2CO_3$ buffer (pH 9.8, adjusted with hydrochloric acid). This solution is emulsified in 15 ml of an organic solvent system consisting of a binary chloroform/cyclohexane (1:4) mixture containing 0.5% of phosphatidylcholine. Controlled stirring corresponding to approximately 500 rpm is maintained for approximately 60 seconds.

To this emulsion thus obtained, 15 ml of a 1.25–2.5% strength solution of terephthaloyl chloride in the same chloroform/cyclohexane (1:4) solvent system are added.

Crosslinking of the serum albumin dissolved in the droplets of dispersed buffer takes place at the interface with the chloroform/cyclohexane solvent system. The crosslinking reaction is continued under these conditions for approximately 60 minutes. The suspension of microcapsules is then diluted with 30 ml of the same solvent system in order to stop the crosslinking.

After removal of the supernatant, the microcapsules are rinsed first with a solution of glycerine containing 25% of polysorbate 20, and then with water. Several successive washings are then carried out, for example using 5 times 50 ml of water/alcohol solutions, or optionally absolute alcohol. The microcapsules thus washed are immersed for at least 12 hours in alcohol, preferably absolute, for example ethyl alcohol.

The microcapsules thus obtained are then charged with active principle by a simple operation of controlled immersion of the microcapsules in a titrated solution of the drug.

The pharmaceutically active substance adsorbed by the walls of the microcapsules preferably consists of a water-soluble compound having a molecular weight substantially between 300 and 600 and bearing an electrical charge.

By way of a particular example of pharmaceutically active substances which can be adsorbed on the walls of the microcapsules according to the present invention, doxorubicin may be mentioned, preferably used in the form of its hydrochloride.

Such a drug may, in particular, be used in the field of chemoembolization. The invention is nevertheless not limited to the use of this particular drug, and other active principles, especially those having antineoplastic activity, can also be incorporated in the microcapsules.

In practice, the release of the active principle from these charged microcapsules proved to be rapid and to be accomplished by diffusion. The rate of release is reduced exclusively with active principles the molecular weight of which is greater than 1000 daltons. It is useful to note that the adsorption and incorporation capacity of the microcapsules of the present invention increases when the rate of biodegradation increases.

STUDY ON BIODEGRADABILITY

The preliminary study of biodegradability was carried out on three dogs, using the method described by Madoulé Ph., Trampont Ph., Quillard J., Doyan D., Lanol-Jeantet M., Zouai O., and Tilleul P., Expérimentation de nouveaux matériaux d'embolisation, Sci., Tech., Pharm., vol. II no. 10, 10, 441–445, 1982.

The dogs were embolized at the left kidney with microcapsules of the present invention, the right kidneys serving as controls. With weakly crosslinked microcapsules, obtained in particular with a serum albumin/crosslinking agent ratio of between 1:0.7 and 1:0.2, the results observed 7 days after embolization show that there is good revascularization due to complete degradation of the microcapsules within this 7 day period. After a longer period of about 10 days, revascularization is complete and the kidney becomes functional again. After the dog is sacrificed and histological analysis performed, there is no abnormality to be reported, with the exception of a small hemorrhagic zone situated at the level of the upper pole of the kidney. By way of comparison, by using fully crosslinked microcapsules of serum albumin, only after a period of about 15 days is revascularization initiated, which indicates the start of degradation in vivo of the microcapsules.

After the animals are sacrificed and histological analysis of the kidney performed, a reduction in the volume of the upper pole of the kidney and an increase in the volume of the lower pole are observed, with substantial hemorrhagic zones within the kidney. These comparative observations show the decisive advantage of the microcapsules which are the subject of the present invention, relatively to the fully crosslinked microcapsules of the prior art.

STUDY OF THE INTERNAL STRUCTURE OF THE MICROCAPSULES

This study was performed by means of scanning electron microscopy.

The structure is a reservoir system, consisting of a wall of partially crosslinked serum albumin bounding a cavity.

STUDY OF THE ADSORPTION OF DRUGS ONTO THE MICROCAPSULES

1. Method 100 mg of microcapsules are suspended in 125 ml of a solution of adriamycin hydrochloride. The medium is stirred at 200 rpm. The apparatus is kept shielded from the light. The adsorption of adriamycin onto the microcapsules is followed by a decrease in the concentration of the drug in the supernatant (spectrophotometry at 492 nm).

2. Results

From a solution of adriamycin hydrochloride of concentration of 0.2 mg/ml, the microcapsules as described bind 90% to 95% of the drug in one hour.

A degree of crosslinking greater than 0.250 g of terephthaloyl chloride per 1 g of albumin does not permit this binding to take place. Furthermore, for a degree of crosslinking of 0.250 g of terephthaloyl chloride per 1 g of albumin, the interfacial polycondensation time has a large influence. A polymerization time of between 30 and 60 minutes permits binding of 90 to 95% of adriamycin hydrochloride in one hour. A polymerization time of 90 minutes only permits binding of 16% of the drug in the same time (1 hour).

Also under the same conditions, these microcapsules bind small inorganic ions such as calcium ($Ca^{++}$). These ions must, however, be positively charged. A thiocyanate ion ($S=C=N^-$), for example, is not adsorbed onto these particles.

STUDY OF THE RELEASE IN VITRO OF DRUGS FROM THE MICROCAPSULES OF SERUM ALBUMIN

1. Method 100 mg of microcapsules charged with adriamycin are suspended in 250 ml of dissolution medium with stirring (100 rpm), at room temperature and shaded from the light. The presence of the drug in the dissolution medium is followed by spectrophotometry at 492 nm.

2. Results

The microcapsules were suspended: 1—in distilled water; 2—in physiological saline (0.9% NaCl). In distilled water, less than 5% of the drug is released into the aqueous phase in 24 hours. The presence of a salt such as sodium chloride enables the adriamycin to be released in a period of 10 hours. The total amount of drug released per 100 mg of microcapsules depends on the volume of physiological saline as a releasing medium (Table 1).

TABLE 1

| Influence of the volume of the dissolution medium on the amount of adriamycin released from microcapsules of serum albumin | |
|---|---|
| Volume of 0.9% strength NaCl solution (ml) | Amount of adriamycin released (%) from the microcapsules of serum albumin |
| 250 | 55.0 |
| 500 | 70.5 |
| 1000 | 81.3 |

TABLE 1-continued

As regards the experiments on release in vitro, the behavior of adriamycin towards the microcapsules shows that the adsorption sites of the microcapsules are negatively charged.

Furthermore, the studies on adsorption of adriamycin show clearly that the degree of crosslinking of the wall has a considerable influence on the penetration of the drug into the wall of the microcapsules. These observations lead to the conclusion that these microcapsules behave as ion exchange resins towards the drugs which are intended to be carried.

We claim:

1. Process for preparing microcapsules containing a pharmaceutically active substance, wherein the mcrocapsules are prepared from serum albumin by carrying out the following successive operations:
    (a) the serum albumin is emulsified by dispersion in an organic solvent system, by adding a pharmaceutically acceptable emulsifying agent, and stirring;
    (b) to the emulsion thereby obtained, maintained stirred, a crosslinking agent dissolved in the said organic solvent system is added, and stirring is maintained until the desired degree of interfacial crosslinking is obtained;
    (c) the microcapsules are isolated after dilution of the reaction mixture followed by a succession of stages of washing with suitable solvents and decantation stages, and the microcapsules are then subjected to several washes with alcohol and to immersion in alcohol, preferably absolute, for at least 12 hours in order to denature the non-crosslinked serum albumin, and
    (d) after the microcapsules are dried, the pharmaceutically active substance is incorporated therein by controlled immersion of the microcapsules in a titrated solution of the said substrate.

2. Process as claimed in claim 1, wherein the microcapsules are isolated by carrying out the following successive operations:
    the supernatant is separated;
    at least one washing of the microcapsules is carried out using the said organic solvent system;
    ⅓ of glycerine containing approximately 25% of polysorbate and then ⅔ of water are added to the microcapsules in that order;
    the microcapsules are separated by sedimentation, before being washed with alcohol and immersed in alcohol.

3. Process as claimed in claim 1 wherein the emulsifying agent is phosphatidylcholine.

4. Process as claimed in claim 1 wherein the organic solvent system consists of a binary mixture of a chlorinated $C_1$ or $C_2$ hydrocarbon and a non-chlorinated $C_5$ to $C_7$ hydrocarbon.

5. Process as claimed in claim 4, wherein the organic solvent system consists of a mixture of chloroform and cyclohexane.

6. Process as claimed in claim 1 wherein the crosslinking agent is an acylating bifunctional reagent, such as a dicarboxylic acid halide or a diisocyanate, in which the two functional groups are both carried on an aromatic ring, or alternatively are separated by an aliphatic chain of 2 to 10 carbon atoms, or one of which is carried on an aromatic ring and the other on an aliphatic chain attached to the ring.

7. Process as claimed in claim 6, wherein the crosslinking agent is selected from the group consisting of succinyl dichloride, sebocoyl dichloride, terephthaloyl dichloride, toluene diisocyanate and hexamethylene diisocyanate.

8. Process as claimed in claim 1 wherein the interfacial crosslinking time is between about 30 minutes and about 90 minutes.

9. Process as claimed in claim 8, wherein the interfacial crosslinking time is about 60 minutes.

10. Process as claimed in claim 1 wherein the ratio by weight of the serum albumin to the crosslinking agent is chosen such that:

$$\frac{1}{1.250} \leq \frac{\text{serum albumin}}{\text{crosslinking agent}} \leq \frac{1}{0.2}$$

11. Process as claimed in claim 10, wherein the ratio by weight of the serum albumin to the crosslinking agent is chosen such that:

$$\frac{1}{0.7} \leq \frac{\text{serum albumin}}{\text{crosslinking agent}} \leq \frac{1}{0.2}$$

12. Process as claimed in claim 1 wherein the alcohol used for the operations of washing and immersion of the microcapsules consists of ethyl alcohol.

13. Process as claimed in claim 1 wherein the microcapsules are recovered in the dry state by evaporation of the washing solvent or solvents.

14. Process as claimed in claim 1 wherein, after they are separated, the microcapsules are subjected to a sterilization operation, preferably radiosterilization by application of radiation of approximately 2.5 Mrad.

15. Process as claimed in claim 1 wherein the pharmaceutically active substance adsorbed by the wall of the microcapsules consists of a watersoluble compound having a molecular weight of substantially between 300 and 600 and bearing an electrical charge.

16. Process as claimed in claim 15, wherein the pharmaceutically active substance is doxorubicin, preferably in the form of its hydrochloride.

* * * * *